United States Patent [19]

Mowrey-McKee et al.

[11] Patent Number: 5,096,607
[45] Date of Patent: Mar. 17, 1992

[54] METHOD FOR CLEANING AND DISINFECTING CONTACT LENSES

[75] Inventors: Mary F. Mowrey-McKee, Victor; David W. Proud, Rochester; George E. Minno, Victor, all of N.Y.

[73] Assignee: Bausch & Lomb Incorporated, Rochester, N.Y.

[21] Appl. No.: 515,290

[22] Filed: Apr. 27, 1990

Related U.S. Application Data

[63] Continuation-in-part of Ser. No. 313,643, Feb. 21, 1989, abandoned.

[51] Int. Cl.$^5$ ................................. C11D 3/48
[52] U.S. Cl. .................. 252/106; 252/174.12; 252/547; 252/DIG. 12; 252/DIG. 14
[58] Field of Search .............. 252/106, 174.12, 547, 252/DIG. 12, DIG. 14; 424/839, 840

[56] References Cited

U.S. PATENT DOCUMENTS

| | | | |
|---|---|---|---|
| 3,910,296 | 10/1975 | Karageozian et al. | 134/2 |
| 4,361,548 | 11/1982 | Smith et al. | 424/78 |
| 4,670,178 | 6/1987 | Huth et al. | 252/95 |
| 4,836,986 | 6/1989 | Ogunbiyi et al. | 422/28 |
| 4,921,630 | 5/1990 | Bhatia | 252/174.12 |

FOREIGN PATENT DOCUMENTS

| | | |
|---|---|---|
| 1150907 | 8/1983 | Canada . |
| 140669 | 10/1984 | European Pat. Off. . |
| 079185 | 5/1985 | European Pat. Off. . |
| 180309 | 9/1985 | European Pat. Off. . |
| 279401 | 2/1988 | European Pat. Off. . |
| 2854278 | 7/1980 | Fed. Rep. of Germany . |
| 57-2457 | 5/1982 | Japan . |
| 57-24526 | 5/1982 | Japan . |
| 116319 | 7/1982 | Japan . |
| 8704091 | 7/1987 | World Int. Prop. O. . |
| 89/11878 | 12/1989 | World Int. Prop. O. . |

*Primary Examiner*—Paul Lieberman
*Assistant Examiner*—Mary DiNunzio
*Attorney, Agent, or Firm*—Salvatore P. Pace

[57] ABSTRACT

Contact lenses are simultaneously cleaned and disinfected by contacting the lenses with an aqueous system containing an antimicrobial agent and a proteolytic enzyme for a period sufficient to clean and disinfect the lenses. The aqueous solutions have suitable osmotic values which do not substantially inhibit the activity of the antimicrobial agent.

20 Claims, No Drawings

METHOD FOR CLEANING AND DISINFECTING CONTACT LENSES

CROSS-REFERENCE TO RELATED APPLICATION

This application is a continuation-in-part of U.S. application Ser. No. 313,643 filed Feb. 21, 1989, now abandoned.

BACKGROUND OF THE INVENTION

1. Field of the Invention

This invention relates to a method for cleaning and disinfecting contact lenses and a composition for the same. More specifically, the present invention is directed to a method for simultaneously cleaning and disinfecting contact lenses by contacting the lenses with an aqueous system containing an antimicrobial agent and a proteolytic enzyme. A composition for simultaneously cleaning and disinfecting the lenses is also provided.

2. Description of Art

In the normal course of wearing contact lenses, tear film and debris consisting of proteinaceous, oily, sebaceous, and related organic matter have a tendency to deposit and build up on lens surfaces. As part of the routine care regimen, contact lenses must be cleaned to remove these tear film deposits and debris. If these deposits are not properly removed, both the wettability and optical clarity of the lenses is substantially reduced causing discomfort for the wearer.

Further, contact lenses, especially those made from hydrophilic materials, must be continuously disinfected to kill any harmful microorganisms that may be present or grow on the lenses. A number of methods for disinfecting contact lenses have been used such as the use of high temperatures, the use of oxidative chemicals, and the use of antimicrobial agents. However, current disinfecting solutions do not exhibit significant cleaning ability for the removal of proteinaceous material.

Conventionally, the cleaning of contact lenses is accomplished with one or both of two general classes of cleaners. Surfactant cleaners, generally known as "daily cleaners" because of their recommended daily use, are effective for the removal of most carbohydrate and lipid derived matter. However, they are not as effective for the removal of proteinaceous matter such as lysozyme. Typically, proteolytic enzymes derived from plant, animal, and microbial sources are used to remove the proteinaceous deposits. These "enzyme" cleaners are recommended for weekly use and are conventionally employed by dissolving enzyme tablets in suitable aqueous solutions.

The process of cleaning and disinfecting contact lenses with enzyme cleaners (as well as daily cleaners) involves two steps. The first step consists of the cleaning phase whereby lenses are conventionally soaked in an enzyme cleaning solution at ambient temperature conditions, i.e., cold soaking for a period of up to 12 hours, to achieve effective removal of proteinaceous deposits. At the conclusion of the cleaning step, the lenses are separately disinfected. Disinfection involves contacting the lenses with a solution containing either an oxidative chemical or an antimicrobial agent at ambient temperatures or exposing the lenses to elevated temperatures for specified periods of time. The latter disinfection technique requires specific electrical disinfecting apparatus.

New methods have been developed which can remove proteinaceous material from contact lenses while disinfecting the lenses. For example, U.S. Pat. No. 4,614,549 discloses a single-step method of cleaning and disinfecting contact lenses in aqueous solutions of proteolytic enzymes at temperatures of between 60° C. and 100° C. This method requires the use of electrical disinfecting apparatus and elevated temperatures. U.S. Pat. No. Re. 32,672 discloses a method which immerses the lenses in a solution containing peroxide and a peroxide-active enzyme. However, this method requires an additional step for the neutralization of the residual peroxide prior to inserting the lens into the eye.

In order to develop an improved simultaneous cleaning and disinfecting method that does not require neutralization of any oxidative chemical, proteolytic enzymes in tablet form were tested in combination with a disinfecting solution containing hexamethylene biguanide polymers as the antimicrobial agent at ambient conditions. However, subsequent microbicidal efficacy studies revealed that the antimicrobial agent was rendered less effective for killing certain microorganisms during these initial studies.

However, it has now been discovered that the disinfecting ability of antimicrobial agents, particularly at ambient temperatures, is most effective under conditions of suitable osmolality for the agent employed. When the osmotic level of the solution is too high, the antimicrobial agents are rendered less effective for killing certain microorganisms.

Thus, according to this invention, proteolytic enzymes can be used in combination with antimicrobial agents to simultaneously clean and disinfect contact lenses. Under ambient temperatures, the disinfection has been found to be most effective at suitable osmotic conditions. The present invention provides a less complex and more convenient regimen for cleaning and disinfecting contact lenses without the need for a separate neutralizing step or electrical disinfecting apparatus.

SUMMARY OF THE INVENTION

According to this invention, a method for simultaneously cleaning and disinfecting contact lenses is provided comprising contacting the lenses with an aqueous system containing an antimicrobial agent and a proteolytic enzyme for a time sufficient to clean and disinfect the lenses wherein the aqueous system has an osmotic value which does not substantially inhibit the activity of the antimicrobial agent.

Also provided is a composition for simultaneously cleaning and disinfecting contact lenses containing an antimicrobial agent and a proteolytic enzyme wherein the final osmotic value of the composition is less than about 800 mOsm./kg. water.

DETAILED DESCRIPTION OF THE INVENTION

The present invention can be used with all contact lenses such as conventional hard, soft, rigid gas permeable, and silicone lenses but is preferably employed with soft lenses such as those commonly referred to as hydrogel lenses prepared from monomers such as hydroxyethylmethacrylate, hydroxyethylmethyl methacrylate, vinylpyrrolidone, glycerolmethacrylate, methacrylic acid or acid esters an the like. Hydrogel lenses typically absorb significant amounts of water such as from 4 to 80 percent by weight.

The compositions employed herein for the cleaning and disinfecting of contact lenses are composed of at least water, one or more proteolytic enzymes, and one or more antimicrobial agents. Generally, these cleaning and disinfecting systems are prepared by mixing two components, the enzyme and a disinfecting solution containing the antimicrobial agents. However, other methods of combining the active components as well as off the shelf compositions containing all of the active components are contemplated as being within the scope of this invention.

A wide variety of proteolytic enzymes are useful in the present invention such as those derived from plant, animal, and microbial sources. The separation and purification of these enzymes is well known to those skilled in the art with many of these enzymes being commercially available. Moreover, it is anticipated that many of the enzymes can be prepared from new techniques being developed such as those using recombinant DNA techniques and proteolytic enzymes prepared by these techniques are contemplated to be within the scope of the present invention.

The proteolytic enzymes used herein must have at least a partial capability to hydrolyze peptide-amide bonds which reduces the proteinaceous material to smaller water-soluble subunits. Typically, these enzymes will exhibit some lipolytic, amylolytic or related activities associated with the proteolytic activity and may be neutral, acidic or alkaline. In addition, separate lipases or carbohydrases may be used in combination with the proteolytic enzymes.

Examples of suitable proteolytic enzymes include but are not limited to pancreatin, trypsin, chymotrypsin, collagenase, papain, bromelain, aminopeptidase, Aspergillo peptidase, pronase E (from *S. graseus*) and dispase (from *Bacillus polymyxa*). The preferred group of proteolytic enzymes are the microbial derived enzymes such as those derived from Bacillus, Streptomyces, and Aspergillus microorganisms. Most preferred are the Bacillus derived alkaline proteases generically called subtilisin enzymes. The subtilisin enzymes include both subclasses, subtilisin A and subtilisin B. Microbial derived enzymes are disclosed in U.S. Pat. No. 4,690,773 incorporated herein by reference.

The present invention employs an effective amount of enzyme to clean the lenses. An effective amount is that which removes a substantial portion of the proteinaceous deposits which occur during normal wear in a reasonable time. The precise amount of enzyme required to make an effective cleaner will depend on several factors including the activity of the enzyme, the purity of the enzyme, the amount of proteinaceous matter deposited on the lenses, the desired soaking period, the specific type of lenses, as well as other factors.

It should be appreciated to one skilled in the art, that the enzyme concentrations useful herein are adjusted depending upon the time allowed for removing the proteinaceous material, the other components in the solutions and the factors previously mentioned. Typically, when the enzyme is provided in solid form, it will be present in amounts from about 0.01 to about 200 milligrams.

Enzyme activity is generally pH dependent and there will be a particular pH range in which any particular enzyme will function best. However, the determination of an optimum pH range can readily be determined by known techniques by those skilled in the art. It is preferred that the enzyme be selected to have substantial activity at a pH between about 6.5 and about 8.5.

The enzyme may be employed in liquid or solid form usually in combination with additional components. Preferably, the enzymes are provided in solid form such as tablets or powders which are mixed with the aqueous solutions prior to use.

Additional components may be added to or incorporated into the enzyme which do not substantially decrease the activity of the enzyme. For example, components such as effervescing agents, stabilizers, buffering agents, chelating and/or sequestering agents, coloring agents, tonicity adjusting agents, surfactants and the like can be employed. In addition, binders, lubricants, carriers, and other excipients normally used in producing tablets may be incorporated into the enzyme when tablets are employed.

Examples of suitable buffering agents which may be incorporated into the enzyme include, but are not limited to, alkali metal salts such as potassium or sodium carbonates, acetates, borates phosphates, citrates and hydroxides, and weak acids such as acetic and boric acids. Preferred buffering agents are alkali metal borates such as sodium or potassium borates. Additionally, other pH adjusting agents may be employed such as inorganic acids. For example, hydrogen chloride may be employed in concentrations suitable for ophthalmic uses. Generally, buffering agents are present in amounts from about 0.01 to about 2.5 percent by weight/volume (w/v).

Effervescing agents are typically employed when the enzyme is provided in solid form. Examples of suitable effervescing agents include, but are not limited to, tartaric or citric acid used in combination with a suitable alkali metal salt such as sodium carbonate.

The disinfecting solutions used with the present invention may contain any of the above-mentioned enzyme components as well as other components but typically will contain water, the antimicrobial agent, one or more of a suitable buffering agent, chelating and/or sequestering agent, tonicity adjusting agent, the surfactant.

The tonicity adjusting agent which may be a component of the disinfecting solution and may optically be incorporated into the enzyme is employed to adjust the osmotic value of the final cleaning and disinfecting solution to more closely resemble that of human tears and to maintain a suitable level for optimum activity by the antimicrobial agent. Suitable tonicity adjusting agents include, but are not limited to, sodium and potassium chloride, dextrose, calcium and magnesium chloride, the buffering agents listed above are individually used in amounts ranging from about 0.01 to 2.5% (w/v) and preferably, from about 0.5 to about 1.5% (w/v). Most preferably, the tonicity agent will be employed in an amount to provide a final osmotic value of the cleaning and disinfecting solutions of less than about 800 millosmoles/kilogram water (mOsm./kg. water).

Suitable surfactants can be either cationic, anionic, nonionic or amphoteric. Preferred surfactants are neutral or nonionic surfactants which may be present in amounts up to 5% (w/v). Examples of suitable surfactants include, but are not limited to, polyethylene glycol esters of fatty acids, polyoxypropylene ethers of $C_{12}$–$C_{18}$ alkanes and polyoxyethylene, polyoxypropylene block copolymers of ethylene diamine (i.e. poloxamine).

Examples of preferred chelating agents include Ethylenediaminetetraacetic acid (EDTA) and its salts (disodium) which are normally employed in amounts from about 0.025 to about 2.0% (w/v). Other known chelating (or sequestering agents) such as certain polyvinyl alcohols can also be employed.

The disinfecting solutions used with this invention will contain a disinfecting amount of one or more antimicrobial agents which are compatible with and do not precipitate in the presence of the enzymes. As used herein, antimicrobial agents are defined as non-oxidative organic chemicals which derive their antimicrobial activity through a chemical or physicochemical interaction with the organisms. Suitable antimicrobial agents are polymeric quaternary ammonium salts used in ophthalmic applications such as poly[(dimethyliminio)-2-butene-1,4-diyl chloride], [4-tris(2-hydroxyethyl) ammonio]-2-butenyl-w-[tris(2-hydroxyethyl)ammonio]dichloride (chemical registry number 75345-27-6) generally available as polyquaternium 1 ® from ONYX Corporation, benzalkonium halides, and biguanides such as salts of alexidine, alexidine free base, salts of chlorhexidine, hexamethylene biguanides and their polymers. The antimicrobial agents used herein are preferably employed in the absence of mercury-containing compounds such as thimerosal. The salts of alexidine and chlorhexidine can be either organic or inorganic and are typically gluconates, nitrates, acetates, phosphates, sulphates, halides and the like. Preferred antimicrobial agents are the polymeric quaternary ammonium salts used in ophthalmic applications and the biguanides. More preferred are the biguanides with hexamethylene biguanides, their polymers and water-soluble salts being most preferred. Generally, the hexamethylene biguanide polymers, also referred to as polyaminopropyl biguanide (PAPB), have molecular weights of up to about 100,000. Such compounds are known and are disclosed in U.S. Pat. No. 4,758,595 which is incorporated herein by reference.

A disinfecting amount of antimicrobial agent is an amount which will at least partially reduce the microorganism population in the formulations employed. Preferably, a disinfecting amount is that which will reduce the microbial burden by two log orders in four hours and more preferably by one log order in one hour. Most preferably, a disinfecting amount is an amount which will eliminate the microbial burden on a contact lens when used in regimen for the recommended soaking time (FDA Chemical Disinfection Efficacy Test-July, 1985 Contact Lens Solution Draft Guidelines). Typically, such agents are present in concentrations ranging from about 0.00001 to about 0.5% (w/v), and more preferably, from about 0.00003 to about 0.05% (w/v).

As mentioned above, it has been found that the antimicrobial agents at simulated commercial concentrations are rendered less effective in environments having high osmotic values, generally above about 800 mOsm./kg. water at typical commercial concentrations (generally less than about 0.05% (w/v)). This is a particularly important discovery since it is common in the industry to add bulking agents to the active enzyme when used in tablet or powder form. These bulking agents usually increase the osmotic values of the cleaning solutions, often significantly reducing the antimicrobial activity. Further, the various components discussed above, as well as others, may also raise the osmolality of the final formulation.

Moreover, it should also be understood that the particular osmotic value rendering any given antimicrobial agent ineffective will vary from agent to agent. The determination of the suitable osmotic range for any particular antimicrobial agent can be easily determined by routine experimentation by one skilled in the art. However, a preferred range of osmotic values has been found to be less than about 800 mOsm./kg. water and more preferable about 200 to about 600 mOsm./kg. water at antimicrobial agent concentrations of less than about 0.05% (w/v).

During practice of this invention, the enzyme formulation, either in solid or liquid form, is typically dissolved in a predetermined amount of disinfecting solution which may be isotonic or hypotonic, to obtain a cleaning and disinfecting solution having the proper osmotic value. This solution is then contacted with lenses at ambient temperatures for a sufficient time to clean and disinfect.

In a preferred embodiment of the invention, an enzyme tablet is dissolved in an aqueous disinfecting solution containing biguanide as the antimicrobial agent in order to prepare the cleaning and disinfecting solution. The lenses are then contacted with the cleaning and disinfecting solution, preferably by being immersed therein, and remain in contact with the solution for a sufficient period of time to disinfect the lenses. An effective amount of enzyme agent is used such that the time sufficient to disinfect will also be sufficient to substantially remove the proteinaceous deposits. Typically, the cleaning and disinfecting will take less than about 8 hours with about 1 to 4 hours being preferred. Advantageously, the lenses can be removed from the solution and placed directly into the eye without the need for a separate neutralizing step. Preferably, the lenses are rinsed with a suitable isotonic aqueous solution prior to insertion into the eye.

The following detailed examples are presented to illustrate the present invention.

EXAMPLE 1-36

In order to study the antimicrobial efficacy of the compositions of the present invention, several aqueous solutions were prepared and evaluated for the log kill rate of *Serratia marcescens*.

Aqueous solutions were prepared having compositions which simulate commercial disinfecting solutions. All percentages indicated throughout these examples are in weight/volume. Each composition had 0.85% boric acid, 0.09% sodium borate, 1.0% Tetronic ® 1107 (a poloxamine surfactant purchased from BASF Corporation), simulated commercial concentrations of alexidine dihydrochloride, chlorhexidine gluconate, PAPB, polyquaternum 1 ® (purchased from ONYX Corporation), and benzalkonium chloride as he antimicrobial agent respectively and 0.005% of a proteolytic enzyme (subtilisin-A enzyme purchased from NOVO Laboratories, Inc.). The osmolality was varied using sodium chloride as the tonicity adjusting agent. Two separate solutions were tested for each composition. The compositions are shown in Table I.

The microbicidal activity of the above solutions were tested in duplicate by exposing Serratia marcescens at about $1.0 \times 10^6$ to about $1.0 \times 10^7$ colony forming units per milliliter (CFU/ml.) to 10 ml. of each solution at room temperature for 1 hour and 4 hour time intervals. An aliquot of each inoculated sample was removed at 1 and 4 hours and diluted in a neutralizing broth (Dey- Engley) and plated with neutralizing agar. The agar plates were incubated for two days and plate counts were determined to calculate reduction in CFU/ml. for the organism. The calculated log order reductions are shown in Table I.

As can be seen from Table I the log order reductions of the various antimicrobial agents tested were significantly reduced at high osmotic levels.

TABLE I

| EXAMPLE | DISINFECTING AGENT | DISINFECTING SODIUM CHLORIDE % (w/v) | MEASURED OSMOLALITY (mOsm/kg water) | LOG REDUCTION S. MARCESCENS | |
|---|---|---|---|---|---|
| | | | | 1 Hour | 4 Hours |
| 1A | Alexidine 1.0 ppm | 0.20 | 200 | 2.6 | >4.5 |
| B | Alexidine 1.0 ppm | 0.20 | 200 | 2.6 | >4.5 |
| 2A | Alexidine 1.0 ppm | 0.53 | 302 | 1.2 | >4.5 |
| B | Alexidine 1.0 ppm | 0.53 | 302 | 1.2 | >4.5 |
| 3A | Alexidine 1.0 ppm | 0.85 | 404 | 0.5 | >4.5 |
| B | Alexidine 1.0 ppm | 0.85 | 404 | 0.6 | >4.5 |
| 4A | Alexidine 1.0 ppm | 1.15 | 500 | 0.2 | 3.4 |
| B | Alexidine 1.0 ppm | 1.15 | 500 | 0.0 | 3.4 |
| 5A | Alexidine 1.0 ppm | 1.47 | 602 | 0.0 | 1.5 |
| B | Alexidine 1.0 ppm | 1.47 | 602 | 0.0 | 1.6 |
| 6A | Alexidine 1.0 ppm | 2.09 | 800 | 0.0 | 1.1 |
| B | Alexidine 1.0 ppm | 2.09 | 800 | 0.0 | 1.1 |
| 7A | Chlorhex 100 ppm | 0.20 | 202 | >4.5 | >4.5 |
| B | Chlorhex 100 ppm | 0.20 | 202 | >4.5 | >4.5 |
| 8A | Chlorhex 100 ppm | 0.53 | 306 | >4.5 | >4.5 |
| B | Chlorhex 100 ppm | 0.53 | 306 | >4.5 | >4.5 |
| 9A | Chlorhex 100 ppm | 0.85 | 402 | 2.0 | >4.5 |
| B | Chlorhex 100 ppm | 0.85 | 402 | 2.0 | >4.5 |
| 10A | Chlorhex 100 ppm | 1.15 | 501 | 1.0 | >4.5 |
| B | Chlorhex 100 ppm | 1.15 | 501 | 1.4 | >4.5 |
| 11A | Chlorhex 100 ppm | 1.47 | 602 | 1.0 | >4.5 |
| B | Chlorhex 100 ppm | 1.47 | 602 | 1.0 | >4.5 |
| 12A | Chlorhex 100 ppm | 2.09 | 800 | 0.0 | 1.6 |
| B | Chlorhex 100 ppm | 2.09 | 800 | 0.1 | 1.4 |
| 13A | PAPB 1.0 ppm | 0.20 | 199 | >4.5 | >4.5 |
| B | PAPB 1.0 ppm | 0.20 | 199 | >4.5 | >4.5 |
| 14A | PAPB 1.0 ppm | 0.53 | 301 | 4.2 | >4.5 |
| B | PAPB 1.0 ppm | 0.53 | 301 | 4.3 | >4.5 |
| 15A | PAPB 1.0 ppm | 0.85 | 402 | 3.0 | >4.5 |
| B | PAPB 1.0 ppm | 0.85 | 402 | 2.8 | >4.5 |
| 16A | PAPB 1.0 ppm | 1.15 | 501 | 2.7 | >4.5 |
| B | PAPB 1.0 ppm | 1.15 | 501 | 2.7 | >4.5 |
| 17A | PAPB 1.0 ppm | 1.47 | 601 | 1.9 | >4.5 |
| B | PAPB 1.0 ppm | 1.47 | 601 | 2.1 | >4.5 |
| 18A | PAPB 1.0 ppm | 2.09 | 801 | 0.3 | >4.5 |
| B | PAPB 1.0 ppm | 2.09 | 801 | 0.2 | >4.5 |
| 19A | Polyquaternium 1 100 ppm | 0.20 | 200 | 3.9 | >4.5 |
| B | Polyquaternium 1 100 ppm | 0.20 | 200 | 4.2 | >4.5 |
| 20A | Polyquaternium 1 100 ppm | 0.53 | 303 | 2.4 | 3.9 |
| B | Polyquaternium 1 100 ppm | 0.53 | 303 | 2.3 | 4.2 |
| 21A | Polyquaternium 1 100 ppm | 0.85 | 403 | 0.9 | 3.1 |
| B | Polyquaternium 1 100 ppm | 0.85 | 403 | 0.9 | 3.0 |
| 22A | Polyquaternium 1 100 ppm | 1.15 | 502 | 0.6 | 2.6 |
| B | Polyquaternium 1 100 ppm | 1.15 | 502 | 0.5 | 2.4 |
| 23A | Polyquaternium 1 100 ppm | 1.47 | 601 | 0.4 | 2.1 |
| B | Polyquaternium 1 100 ppm | 1.47 | 601 | 0.4 | 2.1 |
| 24A | Polyquaternium 1 100 ppm | 2.09 | 802 | 0.4 | 1.4 |
| B | Polyquaternium 1 100 ppm | 2.09 | 802 | 0.4 | 1.2 |
| 25A | Benzalkonium Chloride 100 ppm | 0.20 | 200 | >4.5 | >4.5 |
| B | Benzalkonium Chloride 100 ppm | 0.20 | 200 | >4.5 | >4.5 |
| 26A | Benzalkonium Chloride 100 ppm | 0.53 | 304 | >4.5 | >4.5 |
| B | Benzalkonium Chloride 100 ppm | 0.53 | 304 | >4.5 | >4.5 |
| 27A | Benzalkonium Chloride 100 ppm | 0.85 | 404 | >4.5 | >4.5 |

TABLE I-continued

| EXAMPLE | DISINFECTING AGENT | DISINFECTING SODIUM CHLORIDE % (w/v) | MEASURED OSMOLALITY (mOsm/kg water) | LOG REDUCTION S. MARCESCENS | |
|---|---|---|---|---|---|
| | | | | 1 Hour | 4 Hours |
| B | Benzalkonium Chloride 100 ppm | 0.85 | 404 | >4.5 | >4.5 |
| 28A | Benzalkonium Chloride 100 ppm | 1.15 | 499 | >4.5 | >4.5 |
| B | Benzalkonium Chloride 100 ppm | 1.15 | 499 | >4.5 | >4.5 |
| 29A | Benzalkonium Chloride 100 ppm | 1.47 | 598 | >4.5 | >4.5 |
| B | Benzalkonium Chloride 100 ppm | 1.47 | 598 | >4.5 | >4.5 |
| 30A | Benzalkonium Chloride 100 ppm | 2.09 | 801 | 2.7 | >4.5 |
| B | Benzalkonium Chloride 100 ppm | 2.09 | 801 | 2.9 | >4.5 |
| 31A | PAPB 0.5 ppm | 0.20 | 204 | 0.1 | 0.2 |
| B | PAPB 0.5 ppm | 0.20 | 204 | 0.0 | 0.3 |
| 32A | PAPB 0.5 ppm | 0.53 | 309 | 1.0 | 2.7 |
| B | PAPB 0.5 ppm | 0.53 | 309 | 1.1 | 2.7 |
| 33A | PAPB 0.5 ppm | 0.85 | 402 | 0.1 | 1.5 |
| B | PAPB 0.5 ppm | 0.85 | 402 | 0.2 | 1.5 |
| 34A | PAPB 0.5 ppm | 1.15 | 509 | −0.1 | 0.2 |
| B | PAPB 0.5 ppm | 1.15 | 509 | −0.1 | 0.2 |
| 35A | PAPB 0.5 ppm | 1.47 | 607 | 0.0 | −0.1 |
| B | PAPB 0.5 ppm | 1.47 | 607 | 0.0 | −0.1 |
| 36A | PAPB 0.5 ppm | 2.09 | 806 | −0.1 | 0.0 |
| B | PAPB 0.5 ppm | 2.09 | 806 | 0.0 | 0.0 |

EXAMPLE 37

In order to study the cleaning efficacy of the present invention, several solutions were prepared and evaluated for removal of lysozyme deposits from contact lenses.

The present light transmission through ten new Bausch & Lomb Soflens® (polymacon) Contact Lenses was read through a uv/vis spectrophotometer at 500 and 280 nanometers (nm). An average transmission value was obtained (Tn) which was used below to calculate percent protein removal. An aqueous solution was prepared containing 0.7% NaCl, 0.22% sodium bicarbonate, 0.17% potassium chloride, 0.0005% calcium chloride and 0.15% lysozyme (3x crystallized from egg white). Five lenses were soaked in the lysozyme solution and heated for about 1 hour at about 90° C. After heating, the lenses were removed, finger rubbed and rinsed with isotonic saline solution to remove any nonbound lysozyme on the lenses. The percent light transmission was taken at 280 and 500 nm (Td).

The lenses were then submerged in 10 ml. of an aqueous solution containing 0.005% of subtilisin-A proteolytic enzyme (from NOVO Laboratories, Inc.) and alexidine dihydrochloride (1 ppm) at osmotic values adjusted to 300 and 600 mOsm./kg. water. The lenses remained in the solution for 1 hour at ambient temperature. The lenses were removed, rubbed and rinsed in an aqueous isotonic solution and soaked in the aqueous isotonic solution for an additional 15 minutes. The percent light transmission was taken at 280 and 500 nm (Te).

The above transmission readings were placed into the following equation at each reading (280 and 500 nm) to determine the percent of lysozyme removed:

$$\% \text{ protein lysozyme removed} = \frac{(Tn - Td) - (Tn - Te)}{(Tn - Td)}$$

The % protein removed at 500 nm (the visual range of light) and at 280 nm (specific for protein) is shown in Table II.

EXAMPLES 38–41

The procedure of Example 37 was repeated except that chlorhexidine gluconate (100 ppm), PAPB (0.5 ppm), polyquaternium 1® (100 ppm), and benzalkonium chloride (100 ppm) were substituted for alexidine dihydrochloride, respectively. The results are shown in Table II.

As can be seen from Table II, the present invention removes proteinaceous deposits from contact lenses. It should be mentioned, that the lysozyme deposition technique used herein results in much more severe protein deposition that occurs during normal wear.

It is to be understood that the subject invention is not limited by the above examples which have been provided merely to demonstrate operability and which do not purport to be wholly definitive of the scope of this invention. The scope of this invention shall include equivalent embodiments, modifications, and variations that fall within the scope of the attached claims.

TABLE II

| PRESERVATIVE | CLEANING OSMOLALITY (mOsm/kg. water) | % PROTEIN REMOVED (500 nm) | % PROTEIN REMOVED (280 nm) |
|---|---|---|---|
| 37. alexidine | | | |
| 1 | 300 | 93.4 | 49.5 |
| 2 | | 76.8 | 35.3 |
| 3 | | 75.0 | 33.3 |
| 4 | | 92.5 | 42.4 |
| 5 | | 57.4 | 35.8 |
| Average | | 79.0 | 39.3 |

TABLE II-continued

| PRESERVATIVE | CLEANING | | |
|---|---|---|---|
| | OSMOLALITY (mOsm/kg. water) | % PROTEIN REMOVED (500 nm) | % PROTEIN REMOVED (280 nm) |
| 1 | 600 | 86.8 | 43.6 |
| 2 | | 45.8 | 11.2 |
| 3 | | 16.7 | 25.0 |
| 4 | | * | 33.3 |
| 5 | | 70.3 | 2.9 |
| Average | | 54.9 | 23.2 |
| 38. chlorhexidine | | | |
| 1 | 300 | 77.1 | ** |
| 2 | | 25.0 | ** |
| 3 | | 64.9 | ** |
| 4 | | 78.9 | ** |
| 5 | | 64.3 | ** |
| Average | | 62.0 | ** |
| 1 | 600 | 71.0 | ** |
| 2 | | 53.8 | ** |
| 3 | | 11.1 | ** |
| 4 | | 79.3 | ** |
| 5 | | 40.0 | ** |
| Average | | 51.0 | ** |
| 39. PAPB | | | |
| 1 | 300 | 64.8 | 48.4 |
| 2 | | 63.9 | 45.1 |
| 3 | | 54.4 | 29.1 |
| 4 | | 41.0 | 26.7 |
| 5 | | 15.8 | 7.3 |
| Average | | 48.0 | 31.3 |
| 1 | 600 | 50.0 | 32.9 |
| 2 | | 68.0 | 27.8 |
| 3 | | 31.2 | 31.1 |
| 4 | | 66.7 | 66.4 |
| 5 | | 66.0 | 45.9 |
| Average | | 56.4 | 40.8 |
| 40. polyquaternium 1 ® | | | |
| 1 | 300 | 95.9 | 71.2 |
| 2 | | 70.0 | 42.2 |
| 3 | | 85.8 | 56.7 |
| 4 | | 50.9 | 21.5 |
| 5 | | 34.1 | 26.2 |
| Average | | 67.3 | 43.6 |
| 1 | 600 | 87.5 | 47.2 |
| 2 | | 75.0 | 45.2 |
| 3 | | 89.5 | 27.1 |
| 4 | | 90.2 | 60.7 |
| 5 | | 88.9 | 30.9 |
| Average | | 86.2 | 42.2 |
| 41. benzalkonium chloride | | | |
| 1 | 300 | 17.4 | 39.5 |
| 2 | | 37.5 | 27.1 |
| 3 | | 46.2 | 37.2 |
| 4 | | 44.0 | 27.2 |
| 5 | | 48.0 | 35.4 |
| Average | | 38.6 | 33.3 |
| 1 | 600 | 50.0 | 44.1 |
| 2 | | 36.4 | 39.8 |
| 3 | | 59.1 | 21.4 |
| 4 | | 8.4 | 20.6 |
| 5 | | 59.4 | 29.8 |
| Average | | 42.7 | 31.1 |

*No protein removal observed
**Chlorhexidine interferes with light transmission at 280 nm

What is claimed:

1. A method for simultaneously cleaning and disinfecting contact lenses comprising contacting the lenses with an aqueous system containing a disinfecting amount of an antimicrobial agent selected from the group consisting of polymeric quaternary ammonium salts used in ophthalmic applications and biguanides, in absence of thimerosal, and an effective amount of a proteolytic enzyme for a time sufficient to simultaneously clean and disinfect the lenses and wherein the osmotic value of said aqueous system, is adjusted to a level which does not substantially inhibit the activity of said antimicrobial agent.

2. The method of claim 1 wherein said antimicrobial agent and said proteolytic enzyme are in an aqueous solution.

3. The method of claim 1 wherein said antimicrobial agent and said proteolytic enzyme are contacted with the lenses at ambient temperatures.

4. The method of claim 1 wherein the osmotic value is less than about 800 mOsm./kg. water.

5. The method of claim 1 wherein said antimicrobial agent is a biguanide.

6. The method of claim 5 wherein said biguanide is hexamethylene biguanide polymer having molecular weights of up to about 100,000.

7. The method of claim 6 wherein said osmotic value is from about 200 to about 600 mOsm./kg. water.

8. The method of claim 1 wherein said proteolytic enzyme is in a powder or tablet form and is dissolved in a disinfecting solution containing water and said antimicrobial agent to prepare said aqueous system.

9. The method of claim 1 wherein said proteolytic enzyme is a subtilisin enzyme.

10. The method of claim 3 wherein said aqueous solution additionally contains a buffering agent.

11. The method of claim 3 wherein said aqueous solution additionally contains a surfactant.

12. A method of simultaneously cleaning and disinfecting contact lenses comprising the steps of:
dissolving an effective amount of a proteolytic enzyme in a disinfecting solution containing, as the antimicrobial agent, from about 0.00001 to about 0.5 percent by weight/volume of a nonoxidative chemical selected from the group consisting of polymeric quaternary ammonium salts used in ophthalmic applications and biguanides and from about 0.01 to about 2.5 percent by weight/volume of a buffering agent and sufficient tonicity adjusting agent to provide said solution with a final osmotic value of less than about 800 mOsm/kg water, and contacting said lenses with said solution for a period of time sufficient to simultaneously clean and disinfect said lenses in the absence of thimerosal.

13. An improved method for cleaning and disinfecting contact lenses with proteolytic enzymes and antimicrobial agents in the absence of thimerosal, the improvement comprising contacting the lenses with an aqueous system containing an effective amount of said enzyme and a disinfecting amount of said antimicrobial agent, said antimicrobial agent being selected from the group consisting of polymeric quaternary ammonium salts used in ophthalmic applications and biguanides, and maintaining the osmotic value of the system, by the addition of a tonicity adjusting agent, at a level which does not substantially inhibit the activity of the antimicrobial agent.

14. The method of claim 13 wherein said osmotic value is less than about 800 mOsm./kg. water.

15. The method of claim 13 wherein said composition is prepared by mixing said proteolytic enzyme in a disinfecting solution containing said antimicrobial agent.

16. The method of claim 15 wherein said antimicrobial agent is present in an amount ranging from about 0.00001 to about 0.5 percent by weight/volume.

17. The method of claim 16 wherein said proteolytic enzyme is in tablet or powder form.

18. The method of claim 17 wherein said proteolytic enzyme is a subtilisin enzyme.

19. The method of claim 18 wherein said antimicrobial agent is a biguanide.

20. The method of claim 19 wherein said biguanide is a polymer of hexamethylene biguanide.

* * * * *

US005096607B1

REEXAMINATION CERTIFICATE (3651st)

United States Patent [19]

Mowrey-McKee et al.

[11] B1 5,096,607

[45] Certificate Issued  Oct. 27, 1998

[54] METHOD FOR CLEANING AND DISINFECTING CONTACT LENSES

[75] Inventors: Mary F. Mowrey-McKee, Victor; David W. Proud, Rochester; George E. Minno, Victor, all of N.Y.

[73] Assignee: Bausch & Lomb Incorporated, Rochester, N.Y.

Reexamination Requests:
No. 90/003,986, Oct. 3, 1995
No. 90/004,599, Apr. 9, 1997

Reexamination Certificate for:
Patent No.: 5,096,607
Issued: Mar. 17, 1992
Appl. No.: 515,290
Filed: Apr. 27, 1990

Related U.S. Application Data

[63] Continuation-in-part of Ser. No. 313,643, Feb. 21, 1989, abandoned.

[51] Int. Cl.$^6$ .............................. C11D 3/48; C11D 3/386; A61L 2/16; G02C 13/00
[52] U.S. Cl. .............................................. 422/28; 510/114
[58] Field of Search ........................ 510/114; 422/28, 422/37; 435/264; 514/839, 840

[56] References Cited

U.S. PATENT DOCUMENTS

| | | | |
|---|---|---|---|
| 4,438,011 | 3/1984 | Howes | 422/37 |
| 4,758,595 | 7/1988 | Ogunbiyi et al. | 424/78.26 |

FOREIGN PATENT DOCUMENTS

30 07 397   9/1988   Germany.

OTHER PUBLICATIONS

Jan. 8, 1998 decision of the Japanese Patent Office board of Appeal.
Apr. 3, 1998 decision of the Opposition Division in Europe.
Block, *Disinfection, Sterilization, and Preservation*, 3rd Edition, Chapter 12 (1983).
Hugo et al., *Pharmaceutical Microbiology*, 4th Edition, Chapters 11 and 12 (1987).
Monkhouse et al., "The Effect of EDTA on the Resistance of *Pseudomonas Aeruginosa* to Benzalkonium Chloride", *Australian J. Pharmacy*, Supp. No. 53, vol. 48, No. 570 (Jun. 30, 1967).
Single-page B&L Brochure Captioned "Attention Contact Lens Wearers" (Copyright 1988).
Photocopy of Side Panels of Box for ReNu® Multi–Purpose Solution (Copyright 1988).
Nov. 11, 1988 "Dear Practitioner" Letter Disseminated by B&L with Attached Brochures.
Circa 1987 B&L Advertisement for Renu® Saline Solution Captioned "New ReNu Saline Solution and New ReNu Disinfecting Solution Featuring Dymed™ . . . ".
Aug. 1987 B&L Publication Announcing Introduction of ReNu® Saline Solution and ReNu® Multi–Action Disinfecting Solution.
L. Grau and R.B. Nelson, "Cleaning Efficacy of Three Disinfection/Enzymatic Cleaning Regimens," *Primary Evidence*, Allergan Optical Report Series #001, Allergan, Inc. (May 1988).
Alcon Fold–Out Pamphlet Titled "The Opti–Soft™ System For Soft (Hydrophilic) Contact Lenses" (Feb. 1986).
Alcon Booklet Titled "The Opti–Soft™ System—A guide to comfortable care of soft (hydrophilic) contact lenses" (Feb. 1986).
Double–Sided Alcon Instruction Sheet Captioned "Instructions for the Opti–Soft™ System" (Feb. 1986).
Alcon Fold–Out Pamphlet Titled "The Opti–Soft® System—Instructions for soft lens wearers" (May 1987).
Alcon Fold–Out Pamphlet Titled "The Opti–Free™ System—Instructions for Soft Lens Wearers" (Sep. 1988).
Appendix to Nov. 1982 Protest Filed by Dr. Thilo & Company in Connection with Opposition to Ludwig, et al. German Patent Application No. 30 07 397.
Jan. 1981 Titmus Eurocon Booklet re TE Contact Lens Care System.
Titmus Eurocon Brochure Providing Product Information and Instructions for Use of TE Protein Remover in TE Contact Lens Care System.
Titmus Eurocon Brochure Titled "*The Solution*, TE Contact Lens Care System".
Product Monograph for TE Protein Remover Prepared by Dr. Gerhard Ludwig.
Titmus Eurocon Package Insert for TE Protein Remover.
Titmus Eurocon Brochure Titled "Finally, a Care System for Hard and Soft Contact Lenses".
Barnes–Hind HydroCurve Bulletin, vol. 1, No. 1, "FDA Approval: Thimerosal–Free Storage & Rinsing Solution!" (Jan. 1984).
Nov. 5, 1996 Statutory Declaration of Kate Ambrus (with attachments), submitted by Allergan in the Australian opposition.
Nov. 5, 1996 Statutory Declaration of Nancy Brady (with attachments), submitted by Allergan in the Australian opposition.
Sep. 27, 1996 Statutory Declaration of Joy T. Barnitz (with attachments), submitted by Bausch & Lomb in the Australian opposition.
Feb. 25, 1997 Statutory Declaration of Noel A. Brennan (with attachments), submitted by Bausch & Lomb in the Australian opposition.
Sep. 27, 1996 Statutory Declaration of Anne Jones (with attachments), submitted by Bausch and Lomb in the Australian opposition.
Alcon's opposition (with attachments) to Bausch & Lomb's Korean Patent Application No. 90–2092.

(List continued on next page.)

*Primary Examiner*—Ardith Hertzog

[57]   ABSTRACT

Contact lenses are simultaneously cleaned and disinfected by contacting the lenses with an aqueous system containing an antimicrobial agent and a proteolytic enzyme for a period sufficient to clean and disinfect the lenses. The aqueous solutions have suitable osmotic values which do not substantially inhibit the activity of the antimicrobial agent.

OTHER PUBLICATIONS

Bausch & Lomb's response (with attachments) to Alcon's opposition to Korean Patent Application No. 90–2092.

Alcon's Dec. 30, 1996 Response to Bausch & Lomb brief in Alcon's Opposition to Bausch & Lomb's European Patent 0384666.

A 281200–517 [1995 and 1996 Micro Test Laboratories Inc. documents].

A 280862–88 [Feb. 16, 1996 Declaration of John G.B. Howes, Ph.D (with attachments), submitted by Alcon in its U.S. Patent Application Serial No. 08/091,509].

A 280889–1156 [Feb. 18, 1996 Declaration of Rainer Sunderdiek, Ph.D. (with attachments), submitted by Alcon in its U.S. Patent Application Serial No. 08/091,509].

Sep. 17, 1997 Decision of A Delegate of the Commissioner of Patents in the Australian opposition filed by Allergan.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–11 and 13–20 is confirmed.

Claim 12 is cancelled.

* * * * *

(12) REEXAMINATION CERTIFICATE (4630th)

United States Patent
Mowrey-McKee et al.

(10) Number: US 5,096,607 C2
(45) Certificate Issued: Aug. 20, 2002

(54) METHOD FOR CLEANING AND DISINFECTING CONTACT LENSES

(75) Inventors: Mary F. Mowrey-McKee, Victor; David W. Proud, Rochester; George E. Minno, Victor, all of NY (US)

(73) Assignee: Bausch & Lomb Incorporated, Rochester, NY (US)

Reexamination Request:
No. 90/006,022, May 25, 2001

Reexamination Certificate for:
Patent No.: 5,096,607
Issued: Mar. 17, 1992
Appl. No.: 07/515,290
Filed: Apr. 27, 1990

Reexamination Certificate B1 issued Oct. 27, 1998

Related U.S. Application Data

(63) Continuation-in-part of application No. 07/313,643, filed on Feb. 21, 1989, now abandoned.

(51) Int. Cl.⁷ .................. A61L 12/14; A61L 2/16; C11D 3/48; C11D 3/386; G02C 13/00
(52) U.S. Cl. ................. 422/28; 510/114; 435/264
(58) Field of Search ......................................... 422/28

(56) References Cited

U.S. PATENT DOCUMENTS

| | | | |
|---|---|---|---|
| 3,689,673 A | 9/1972 | Phares | 424/326 |
| 3,910,296 A | 10/1975 | Karageozian et al. | 134/2 |
| 4,029,817 A | 6/1977 | Blanco et al. | 424/329 |
| 4,525,346 A | 6/1985 | Stark | 424/80 |
| 4,614,549 A | 9/1986 | Ogunbiyi et al. | 134/19 |
| B1 3,910,296 | 4/1987 | Karegeozian et al. | 134/42 |
| 4,690,773 A | 9/1987 | Ogunbiyi et al. | 252/174.12 |
| RE32,672 E | 5/1988 | Huth et al. | 252/95 |
| 4,758,595 A | 7/1988 | Ogunbiyi et al. | 514/635 |

FOREIGN PATENT DOCUMENTS

| | | | |
|---|---|---|---|
| EP | 0 140 669 | 5/1985 | |
| EP | 0 180 309 | 5/1986 | 47/44 |
| JP | 24526 | 5/1982 | |

OTHER PUBLICATIONS

U.S. patent application Ser. No. 451,728, Boghosian, filed Mar. 18, 1974.
Bausch & Lomb literature, "Lens Care Used To Be As Easy As One, Two, Three."
Alcon literature, "The Opti–Soft™ System".
Frederick Segel, *Remington's Pharmaceutical Sciences*, Ch. 80, 1455–65, (Alfonso R. Gennaro ed. 1985).
Alcon Literature, "The Opti–Free System".
Board of Appeals of the Japanese Patent Office decision regarding JPA No. 2–37540 ("Method and Composition for Cleaning and Disinfecting Contact Lenses") with English translation.
Declaration of Stanley W. Huth, dated Aug. 28, 1995.
Statutory Declaration of Kate Ambrus, dated Apr. 2, 1996, with attached Statutory Declaration of Nancy Brady, dated Apr. 11, 1996.
Declaration of Mary Ingram to Accompany Request for Reexamination, dated Nov. 19, 1996.
Declaration of Murray J. Sibley to Accompany Request for Reexamination, dated Mar. 27, 1997.

*Primary Examiner*—E. Leigh McKane

(57) ABSTRACT

Contact lenses are simultaneously cleaned and disinfected by contacting the lenses with an aqueous system containing an antimicrobial agent and a proteolytic enzyme for a period sufficient to clean and disinfect the lenses. The aqueous solutions have suitable osmotic values which do not substantially inhibit the activity of the antimicrobial agent.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–11 and 13–20 is confirmed.

Claim 12 was previously cancelled.

* * * * *